United States Patent
Weiland et al.

(10) Patent No.: US 6,211,952 B1
(45) Date of Patent: Apr. 3, 2001

(54) METHOD AND APPARATUS FOR INSPECTING GLASS CONTAINERS FOR CHECKS

(75) Inventors: Joseph G. Weiland, Valencia; Henry M. Dimmick, Sr., deceased, late of Butler, both of PA (US), by Mary L. Dimmick, executrix

(73) Assignee: AGR International, Inc., Butler, PA (US)

( * ) Notice: Subject to any disclaimer, the term of this patent is extended or adjusted under 35 U.S.C. 154(b) by 0 days.

(21) Appl. No.: 09/165,599

(22) Filed: Oct. 2, 1998

(51) Int. Cl.[7] ..................................... G01N 21/00
(52) U.S. Cl. ................. 356/239.4; 356/240; 356/237
(58) Field of Search .......................... 356/428, 239.4, 356/240, 237

(56) References Cited

U.S. PATENT DOCUMENTS

| | | |
|---|---|---|
| 4,399,357 | 8/1983 | Dorf et al. . |
| 4,418,564 | 12/1983 | McKinley . |
| 4,424,441 | 1/1984 | Bieringer et al. . |
| 4,483,615 | 11/1984 | Bieringer et al. . |
| 4,584,469 | 4/1986 | Lovalenti . |
| 4,651,568 | 3/1987 | Reich et al. . |
| 4,723,448 | 2/1988 | Veligdan . |
| 4,733,973 | 3/1988 | Machak et al. . |
| 4,831,250 | 5/1989 | Fukuchi et al. . |
| 4,865,447 | 9/1989 | Shay . |
| 5,144,124 | 9/1992 | Hansen . |
| 5,305,391 | 4/1994 | Gomibuchi . |

OTHER PUBLICATIONS

Emhart Powers, *Powers Check Detector*, Elmira, New York.
Precision Co., Ltd., *AFCD*, Japan.

*Primary Examiner*—Frank G. Font
*Assistant Examiner*—Reginald A. Ratliff
(74) *Attorney, Agent, or Firm*—Arnold B. Silverman; Brij K. Agarwal; Eckert Seamans Cherin & Mellott, LLC

(57) ABSTRACT

A method and apparatus are provided for inspecting glass containers for checks. The container finish is illuminated from the exterior and light reflected from a check is detected by the apparatus. In one embodiment, the glass container finish is inspected for horizontal and related diagonal checks and, in another, the glass container finish is inspected for vertical and related diagonal checks. The checks redirect the normal beam of light and thereby permit the reflected light to be delivered to a detector which converts the received light into a corresponding electrical signal which is compared to a standard in order to determine whether the container should be rejected. The method eliminates incorrect inspection results due to reflection of light caused by threads, lugs, mold seams, takeout beads and the sealing surface of the container mouth. The vertical and horizontal embodiments may be combined into a single system which inspects for vertical, horizontal and diagonal checks.

92 Claims, 9 Drawing Sheets

METHOD AND APPARATUS FOR INSPECTING GLASS CONTAINERS FOR CHECKS

BACKGROUND OF THE INVENTION

1. Field of the Invention

The present invention relates to a method and associated apparatus for inspecting glass containers for checks and, more specifically, it relates to inspection of glass containers for horizontal checks, vertical checks and diagonal checks.

2. Description of the Prior Art

During the molding of glass containers, such as bottles, for example, checks can be formed in the process. Checks are generally considered to be cracks or other structural weaknesses which may, in some instances, be caused by inadvertent rapid cooling. Other checks may result from folds in the glass that are not hot enough to flow together inside the mold. Checks may also occur during the annealing process which generally takes place immediately after molding. Generally, when checks occur, they tend to occur repeatedly in the same location and orientation on the containers. Also, mold conditions may change even in a minor way and result in new checks appearing.

Checks can cause breakage of glass bottles during storage, filling, shipment, further storage and use. Also, cracks, chips and sharp edges which can result from checks can cause injury to persons handling the bottles or pouring the contents or drinking therefrom.

It has been known to provide check detectors that rely on optical means to identify checks. As checks are abrupt changes in direction in the surface of the glass, they can be detected as bright glints of light from the facets of their irregular surfaces. One of the problems with existing optical systems is that threads, mold seams, takeout rings and sealing surfaces also have corners which can easily be confused for checks.

One known form of check detector is marketed under the trade designation "Powers Check Detector" by Emhart Powers of Elmira, N.Y. It employs the concept of using very localized lighting and detector field of view in order to avoid problems created by threads, mold seams, takeout rings and sealing surfaces. A problem presented by this approach is that the check must first be identified by human visual inspection and then a narrow beam of light and narrow field of view detector positioned so as to reflect light from the check into the detector when the bottle is rotated in the field of view. This type of detection device generally consists of a lens with a single detector such as a silicon photodiode at the focus. Precise positioning of the light source and detector are required so as to avoid receipt of glints from other features of the bottle during rotation. This tends to be a time-consuming process and must be repeated for each check found in the containers. As a result, the container molding system and related equipment is out of service while the operator sets up the detectors. As new checks develop, they will not be detected by the machine until the operator notices them and sets up another light source-detector pair. This not only requires human intervention, but substantially reduces the reliability of the molding operation.

It has also been known to employ machines which purport to inspect the entire container and detect checks with "smart" optics. Such machines have been made available commercially under the trade designation AFCD by Precision Co., Ltd. of Japan. These systems employ computer programs to examine the entire surface of the finish and attempt to distinguish threads and other intentionally provided configurations from undesired checks. A plurality of lights and detectors provide a number of combinations of light-detector pairs. The computer is said to recognize the combinations of glints that are characteristics of threads and other intentionally placed shapes and differentiate them from check glints. Relative rotation is established between a rotating container which may be a bottle under the inspection head or rotation of the inspection head with respect to a stationary bottle.

In spite of the foregoing known systems, there remains a very real and substantial need for a method and associated apparatus which will rapidly and effectively monitor glass container finishes for checks having various orientations.

SUMMARY OF THE INVENTION

The present invention has met the above-described need by providing a method of inspecting glass containers for checks in a rapid, reliable manner and associated apparatus.

In one embodiment, horizontal and certain diagonal checks are inspected for and in another embodiment, vertical and other diagonal checks are inspected for.

The method in one embodiment includes introducing the container into an inspection region, illuminating the exterior of the container around the circumference of the container finish, detecting light reflected in the interior of the container finish and comparing the detected light with a reference standard. On the basis of this comparison, a determination is made as to whether checks exist.

The apparatus includes light source means for delivering a beam of light to reflector means which causes the light beam to impinge on the exterior of the container finish and detector means which receives light reflected from the interior of the container finish and converts it into a corresponding electrical signal which is introduced into a microprocessor for comparison with standard data for the container to determine if the container should be rejected due to the presence of undesired checks. Reject means may be activated by the microprocessor to remove a rejected container.

The light source preferably is a pulsed light source which depending on the embodiment, causes the light to impinge on the container finish from different directions. A preferred approach with respect to horizontal and associated diagonal checks is to have the light impinge generally radially. In the embodiment which monitors vertical and associated diagonal checks, it is preferred to have the light impinge on the container finish generally tangentially. In both embodiments, there will generally be only a circumferential portion of the container finish inspected by the inspection means with a plurality of inspection means being employed to inspect the entire circumference.

In another embodiment, the container may be rotated and only one horizontal detector and one vertical detector employed to inspect the container finish.

In general, the pulsed light will impinge on reflector means and the reflected light will be further reflected so as to deliver it to the detector means which converts the received light into a related electrical signal which is delivered to a microprocessor for purposes of effecting the desired comparison.

It is an object of the present invention to provide a method and apparatus for inspecting glass containers for checks without requiring prior knowledge of the existence of or location of checks.

It is a further object of the invention to provide such a method and apparatus wherein features such as container threads, lugs, mold lines, sealing surfaces and takeout rings, as well as other intentionally provided irregularities in the container finish are excluded from the comparison mechanically, optically, or electrically.

It is a further object of the present invention to provide a plurality of inspection units which cooperate to inspect the full 360 degree circumference of the container, which may be a bottle.

It is a further object of the present invention to provide such a system which will operate at rapid speeds and will automatically determine the presence of one or more checks without requiring human intervention.

It is a further object of the present invention to provide such a system which will automatically reject and physically remove containers having checks which exceed a predetermined threshold.

It is a further object of the present invention to provide such a system wherein horizontal and vertical detectors may be employed to inspect portions of a stationary container which is then rotated so that another portion of the container finish can be inspected.

These and other objects of the invention will be more fully understood from the following description of the invention on reference to the drawings appended hereto.

DESCRIPTION OF THE PREFERRED EMBODIMENTS

As employed herein, the term "checks" means cracks, chips, large bubbles, or other structural defects created during molding, annealing of glass containers or other portions of the container manufacturing process.

As employed herein, the term "glass container" means a glass bottle or jar adapted to contain a product and be sealed by a separate closure.

As employed herein, the term "piping" or "piped" refers to light being reflected within the glass container's walls between the inside and outside surfaces thereof.

As employed herein, the term "container finish" means an annular wall of the container extending from the mouth down (a) to a position below the threads, or lugs, and takeout rings or (b) about 0.75 to 1.0 inches, whichever is greater.

As employed herein, the term "detector means" refers to means for receiving container reflected light and converting the same into a corresponding electrical signals and shall expressly include, but not be limited to electronic cameras, charge coupled devices and photodiode detectors.

Figure 1:
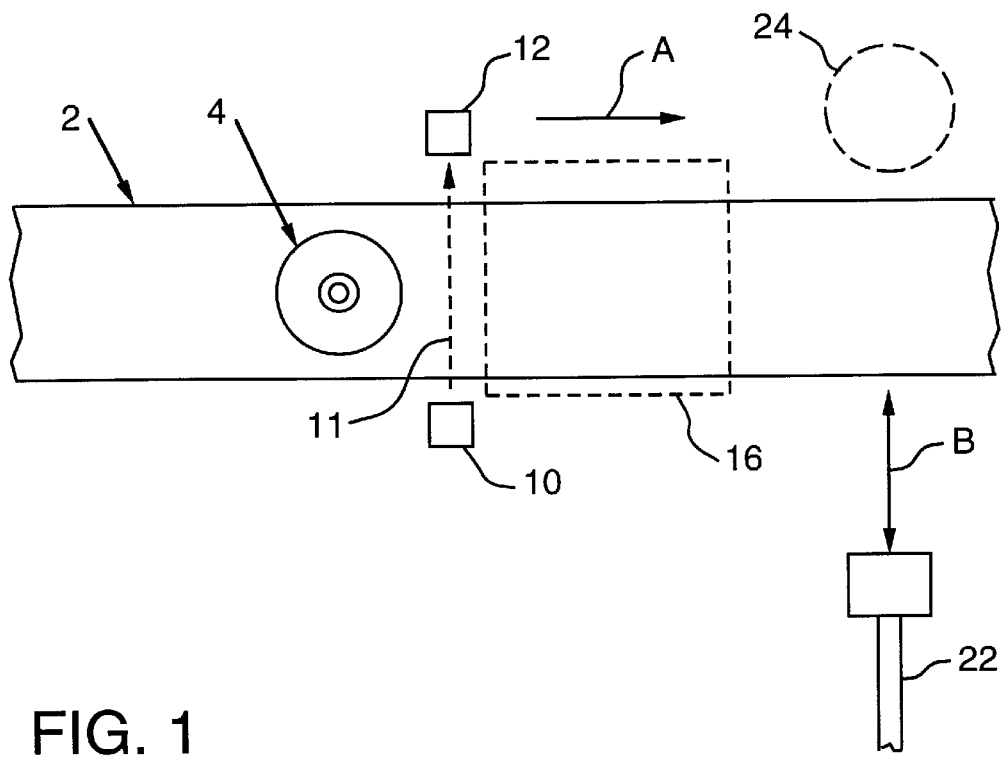
FIG. 1 is a partially schematic plan view of a conveyor transporting a container to be inspected.

FIG. 1 illustrates in top plan view schematically a conveyer 2 which is adapted to transport a plurality of containers 4 in the direction shown by arrow A for check inspection. While for simplicity of illustration, a single container 4 has been shown, it will be appreciated that the process contemplates continuous movement of conveyer 2 such that high speed inspection of the containers may be effected. Containers may be moved on the conveyer on the order of about 600 containers per minute or more. A container sensing station which consists of non-contacting means for confirming that a container 4 is entering the inspection area may be employed. For example, a light source 10 may establish a light beam 11 across the conveyer 2 with a detector 12 determining that a container is present when the light beam is blocked. The detector 12 will then deliver a signal to the microprocessor to initiate inspection of the container. The container 4 will then enter the inspection station 16 which will be discussed in greater detail hereinafter.

In the event that a container is rejected as a result of checks being present at an unacceptable level, a reject mechanism 22, which may be any suitable reject mechanism, is adapted to move in the directions indicated by the double-headed arrow B and physically remove a rejected container, such as 24, from the conveyer 2. In lieu of the illustrated container contacting reject mechanism 22, non-contacting reject mechanisms, such as one which provides one or more jets of air may be used.

Figure 2:
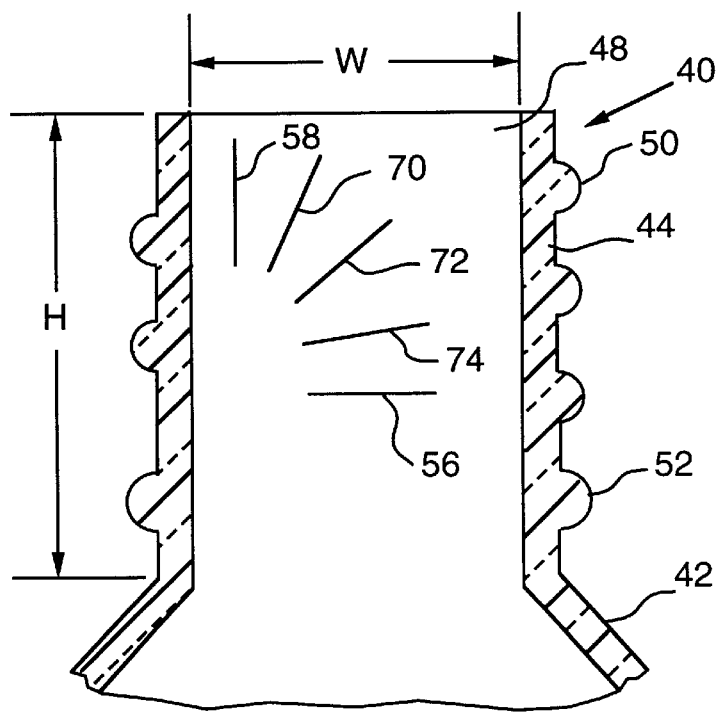
FIG. 2 is a cross-sectional view of a portion of a glass container which may be inspected by a system of the present invention.

FIG. 2 shows the upper portion of a glass container 40 in the form of a bottle having a generally inwardly tapered wall portion 42 and a cylindrical finished portion 44 which terminates at its upper extremity in a bottle mouth 48, having a width W. The container finish 44 has a height H which extends downward below thread 50 and takeout ring 52.

Also shown in FIG. 2, as schematically represented by straight lines, are a series of checks. Check 56 is horizontally oriented, check 58 is vertically oriented, and checks 70, 72, 74 are diagonally oriented.

Referring still to FIG. 2, the present invention provides a method and related apparatus for inspecting, in one embodiment, horizontal checks, such as 56, and related horizontal diagonal checks, such as 74. The vertical embodiment could inspect for check 58 and checks 70, 72. It is preferable to have overlap between horizontal and vertical inspection zones with respect to diagonal checks. For example, horizontal checks and diagonal checks above or below the horizontal up to about 40 degrees therefrom could be inspected by the horizontal inspection unit. In the vertical unit, vertical checks will be inspected as will related vertical diagonal checks being within about 70 degrees of the vertical. This creates a diagonal inspection overlap of about 20 degrees. Different amounts of overlap could be employed, if desired. The use of overlap resists undesired angular gaps which would result in incomplete inspection for diagonal checks. The term "diagonal," when employed in these two contexts, shall refer to angular departures from horizontal or vertical as the case may be. In the preferred embodiment, the inspection will occur only within the glass container finish 44 which, in the form shown, has a height H.

Figure 3:
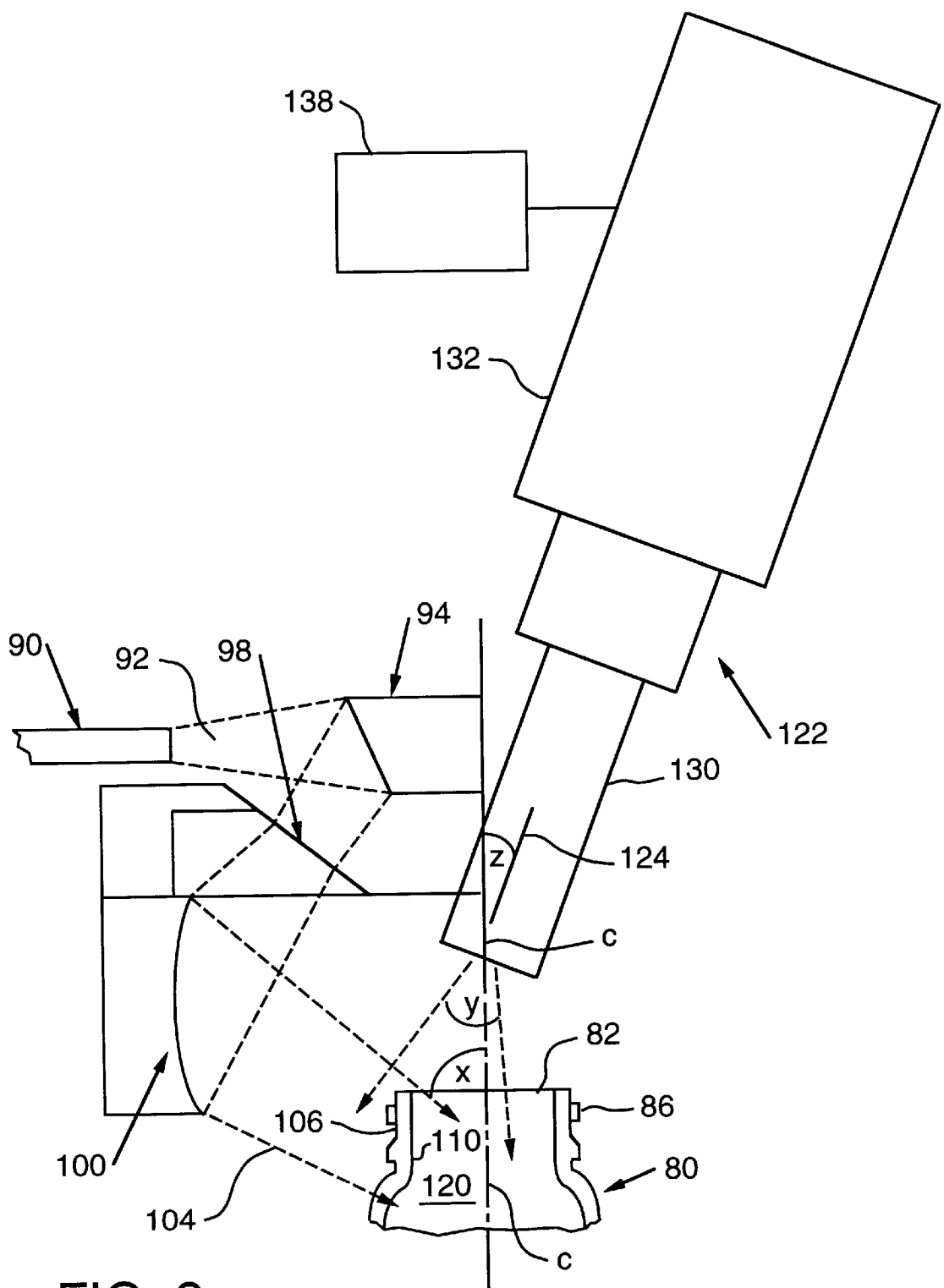
FIG. 3 is a schematic elevational view of a form of inspection apparatus of the present invention suitable for inspecting horizontal and related diagonal checks.

Referring to FIG. 3 a schematic elevational view of an embodiment of the invention adapted to inspect for horizontal checks and related diagonal checks will be considered.

Figure 5:
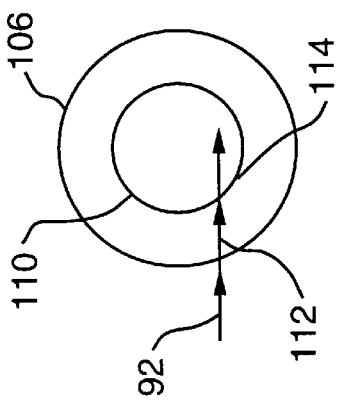
FIG. 5 is a schematic plan view of a portion of a bottle finish being inspected for horizontal checks.

In the form shown, a bottle 80 has a mouth 82, a thread 86, and has its longitudinal axis C oriented generally vertically. A light source 90, which may be a fiber optic bundle, directs a beam of light 92 on conical reflector 94 which is hollow. Reflector 94 has a generally conical configuration such that the conical reflector 94 does not increase the light beam angle in the vertical plane, but does increase it in the horizontal plane. This results in the rectangular beam illuminating the conical diffusion screen 98. The diffusion screen 98 then spreads the light out over toroidal reflector 100. The reflector 94 may be made of any structurally suitable material having the desired reflective properties. It might be made of aluminum or chrome plated plastic or electroformed nickel with a chrome plating, for example. Light beam 104 emerges from the toroidal reflector 100 and impinges on exterior surface 106 of the finish of bottle 80. It preferably impinges generally radially, as viewed in plan. The finish of bottle 80 has an inner surface 110. As shown in FIG. 5, light beam 92 becomes light beam 112 within the container. When the light 112 contacts a check, such as 114, the angle of reflection within the glass is altered in the vertical direction thereby creating a glint which may be detected. It is noted in FIG. 3 that the diffused beam 104 impinges on the glass container 80 from above at a nominal angle X which is preferably about 45 to 55 degrees and is diffused ±40 degrees from the angle X.

The detector means 122 monitors light from the interior 120 of the container finish over an angle Y which is about 60 to 80 degrees with the detector means 132 being disposed above the container 80 and having a central longitudinal axis 124 at an angle Z which is about 0 to 40 degrees and preferably about 25 to 35 degrees with respect to the vertical. The detector means 122 may consist of a lens 130 which converges the reflected light received from the interior of the glass container 80 onto a detector 132 which may, for example, be a charge coupled device, an electronic camera, a single photodiode or multiple photodiodes. The detector 132 converts the reflected light into a corresponding electrical output signals which is delivered to microprocessor 138. Microprocessor 138 compares the received electrical signals with a stored standard value in order to determine whether the container being inspected has checks which exceed the tolerable or threshold amount. If so, a signal is sent from the microprocessor 138 to the reject mechanism 22 (FIG. 1) to reject the container 80. The microprocessor 138 may also, if desired, issue an alarm or shut down the system if the comparison is such as to make such action desirable. The microprocessor 138 will also contain information regarding the different container finishes which will be inspected. This will not only provide the comparison standard data, but will also permit proper automatic positioning of the apparatus with respect to each finish type, if desired.

The conical reflector 94 and toroidal reflector 100, shown in FIG. 3, may be unitary 360 degree reflectors, in which case, it will effect full inspection of the entire circumference of the container finish 106. In the alternative, it may be segmented so as to have a plurality of reflectors each associated with its detector means. In the alternative, subsystems inspecting less than 360 degrees may be employed sequentially to inspect different portions of the circumference of the finish 106. Depending upon positioning of the inspection means, rotation of the container between successive inspection stations may be required.

It will be appreciated that different size conical reflectors 94 and toroidal reflective portions 100 may be employed with different size containers. Also, the microprocessor 138 which may be a suitably programmed general purpose computer would preferably store information regarding each specific container type to be inspected and can be suitably accessed so as to provide the proper comparison between the container being inspected and the stored standard value.

Figure 4:
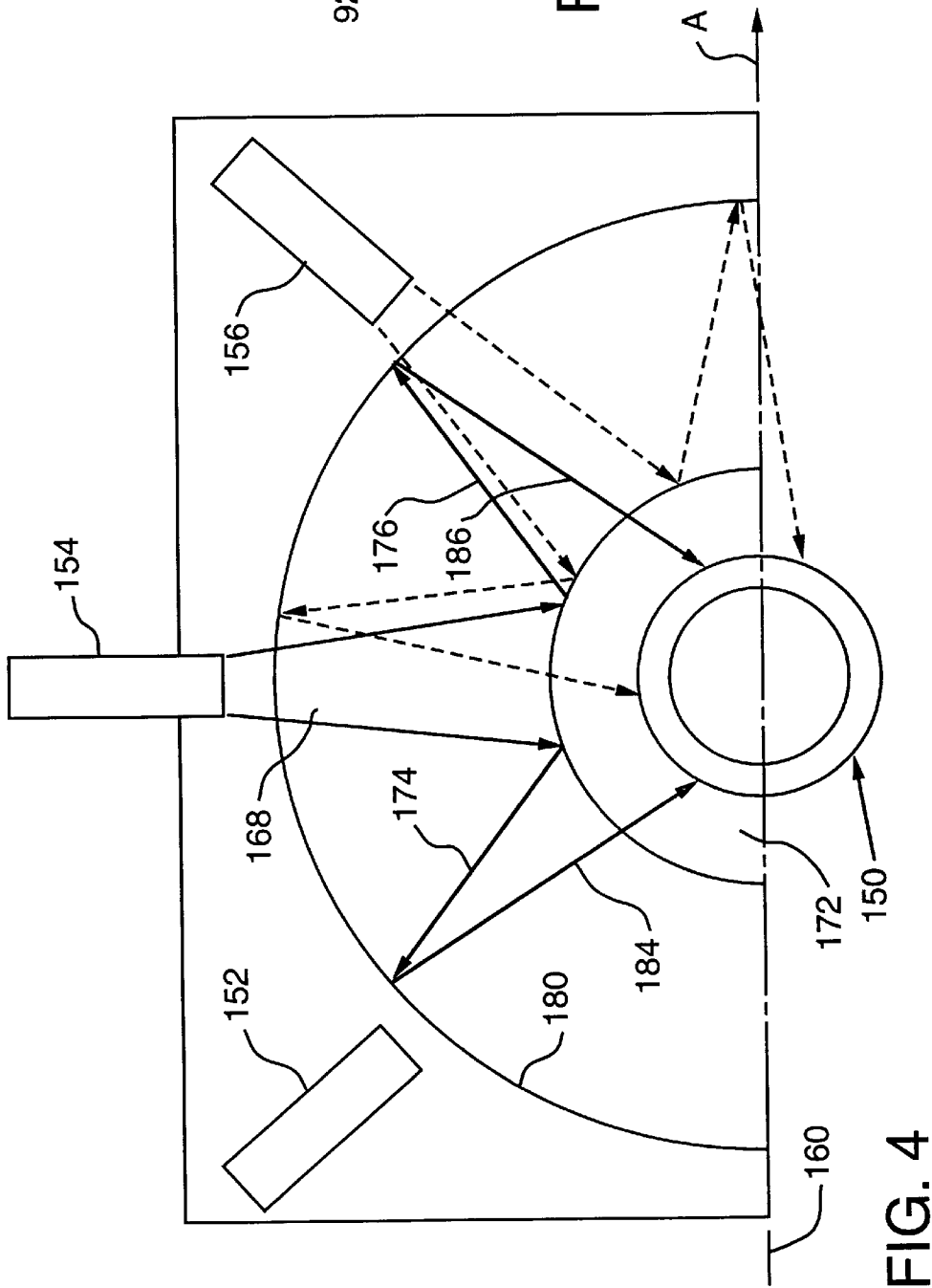
FIG. 4 is a schematic plan view form of inspection system of FIG. 3 without the detector means.

Referring to FIG. 4, the system of FIG. 3 and its horizontal inspection means will be considered in greater detail. A bottle finish 150 receives light generally radially from a plurality of fiberoptic bundles 152, 154, 156. It will be appreciated that this view for convenience of reference shows only 180 degrees of the system which is positioned with respect to conveyor 160 which is transporting bottles in the direction of arrow A. A mirror image portion of the same system would be provided below what is illustrated. Referring specifically to fiberoptic bundle 154, a light beam 168 is directed generally radially toward the conical reflector 172 which, in turn, causes reflected light 174, 176 to engage toroidal reflector 180 which reflects the light 184, 186 generally radially onto the exterior of container finish 150. Similar light beam sequences are provided with respect to the other fiberoptic bundles 152, 156.

Figure 6:
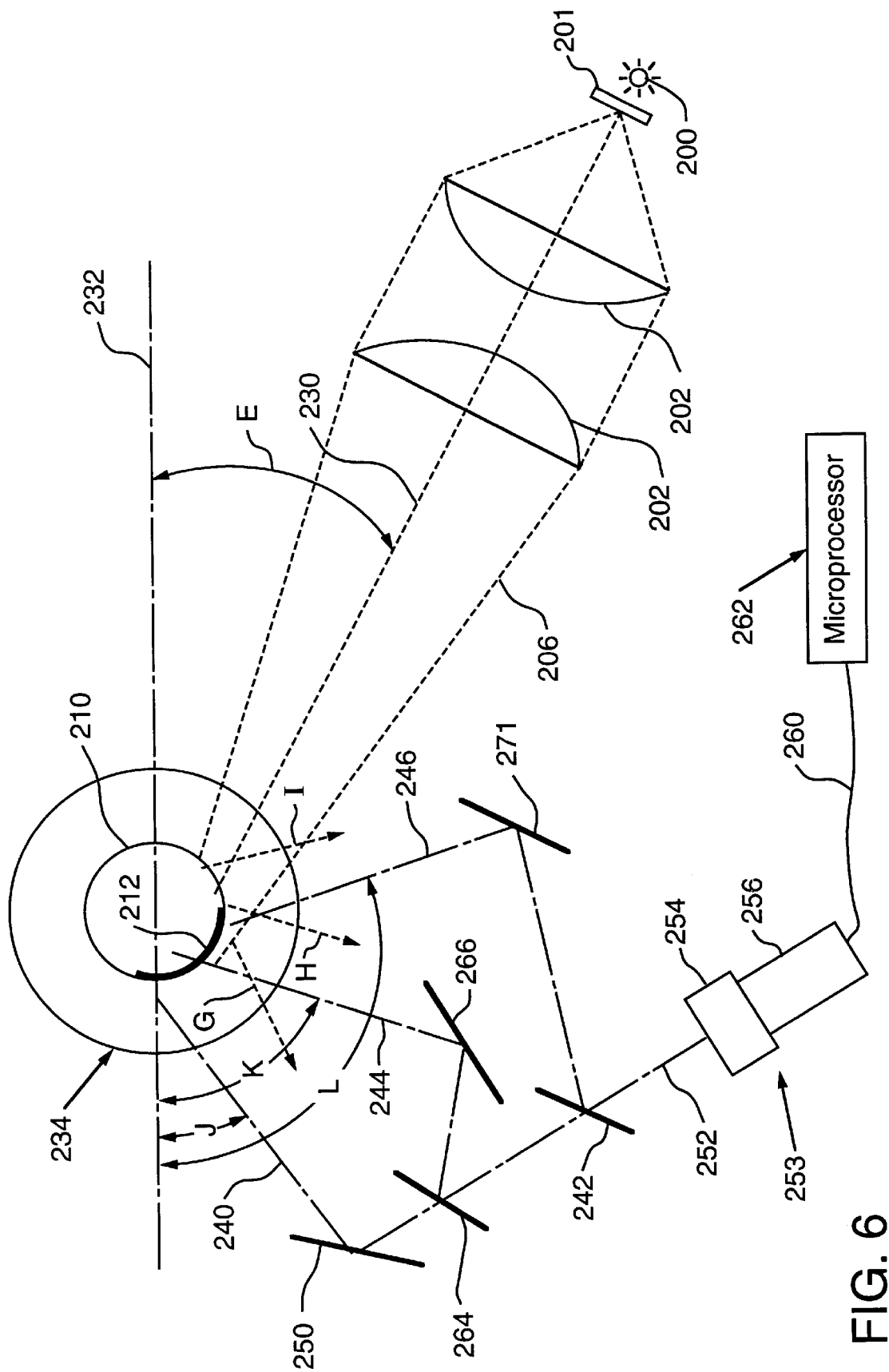
FIG. 6 is a schematic plan view of an embodiment of the present invention suitable for inspecting for vertical and related diagonal checks.

Referring to FIG. 6, an embodiment of the invention employable for checking vertical and related diagonal checks will be considered. It will be appreciated that in this embodiment, the light source 200 illuminates a generally rectangular diffuser 201. Condensing lens 202 will cause the light beam emerging from diffuser 201 to converge and impinge generally tangentially on bottle finish 210 in the region to be inspected indicated generally by the darkened line 212. In the form shown, the centerline 230 of the converging light beam 206 is at an angle E with respect to the centerline 232 of the conveyor which is transporting the bottle 234. This angle may be about 20 to 35 degrees and preferably would be about 25 to 30 degrees. The light beam 206 will impinge simultaneously around the circumference of the container finish 210 through an arc of about 60 to 90 degrees. Light beam 206 will be reflected from checks generally outwardly from the bottle finish 210. Some of the reflected beams will impinge on mirror 250, or mirror 266, or mirror 271. Light beams reflected from mirror 250 are directed through beam splitter 264 and beam splitter 242 as part of beam 252 to the detector means which includes lens 254 and detector means 256. The detector means converts the light into a corresponding electrical signal which will pass over lead 260 to microprocessor 262. Light beams reflected from mirror 266 are reflected from beam splitter 264 and pass through beam splitter 242 as part of beam 252 to the lens 254 and detector means 256 with the detector means converting the light into a corresponding electrical signal which will pass over lead 260 to microprocessor 262.

Light beams reflected from mirror 271 are reflected from beam splitter 242 as part of beam 252 to the lens 254 and detector means 256 with the detector means converting the light into a corresponding electrical signal which will pass over lead 260 to microprocessor 262. The detector circuit may also contain a preamplifier followed by a thresholding circuit in order to establish the threshold for the minimum sized glint that would be detected by the system. When it is desired to detect individual glints from checks, charge coupled devices are a preferred form of detector means. Where the objective is to obtain the cumulative values of all glints from check in the field of view, photodiode detectors are preferred.

Beam splitter 264 may provide a 40/60 split with approximately 40 percent of the light being reflected and approximately 60 percent being transmitted. Beam splitter 242 may provide a 30/70 split with approximately 30 percent of the light being reflected and approximately 70 percent being transmitted.

Mirrors 250, 266, and 271 are positioned so that light beams G or H or I, which are first surface reflections from the outside of the finish, will not be reflected into the lens 254 and onto the detector means 256.

It will be appreciated that mirrors 250, 266, and 271, along with beam splitters 242 and 264, combine three fields of view, whose centerlines are along beam 240, 244, 246 into one field of view whose centerline is along beam 252. It will also be appreciated that, in this embodiment, beam 240 makes a preferred angle J of 35 degrees with respect to centerline 232 of the conveyor, beam 244 makes a preferred angle K of 72 degrees with respect to centerline 232 of the conveyor, and beam 246 makes a preferred angle L of 109 degrees with respect to centerline 232 of the conveyor. A plurality of systems of the type shown in FIG. 6 or rotation of the bottle would be employed to inspect the complete circumference of the container finish 210.

Figure 7:
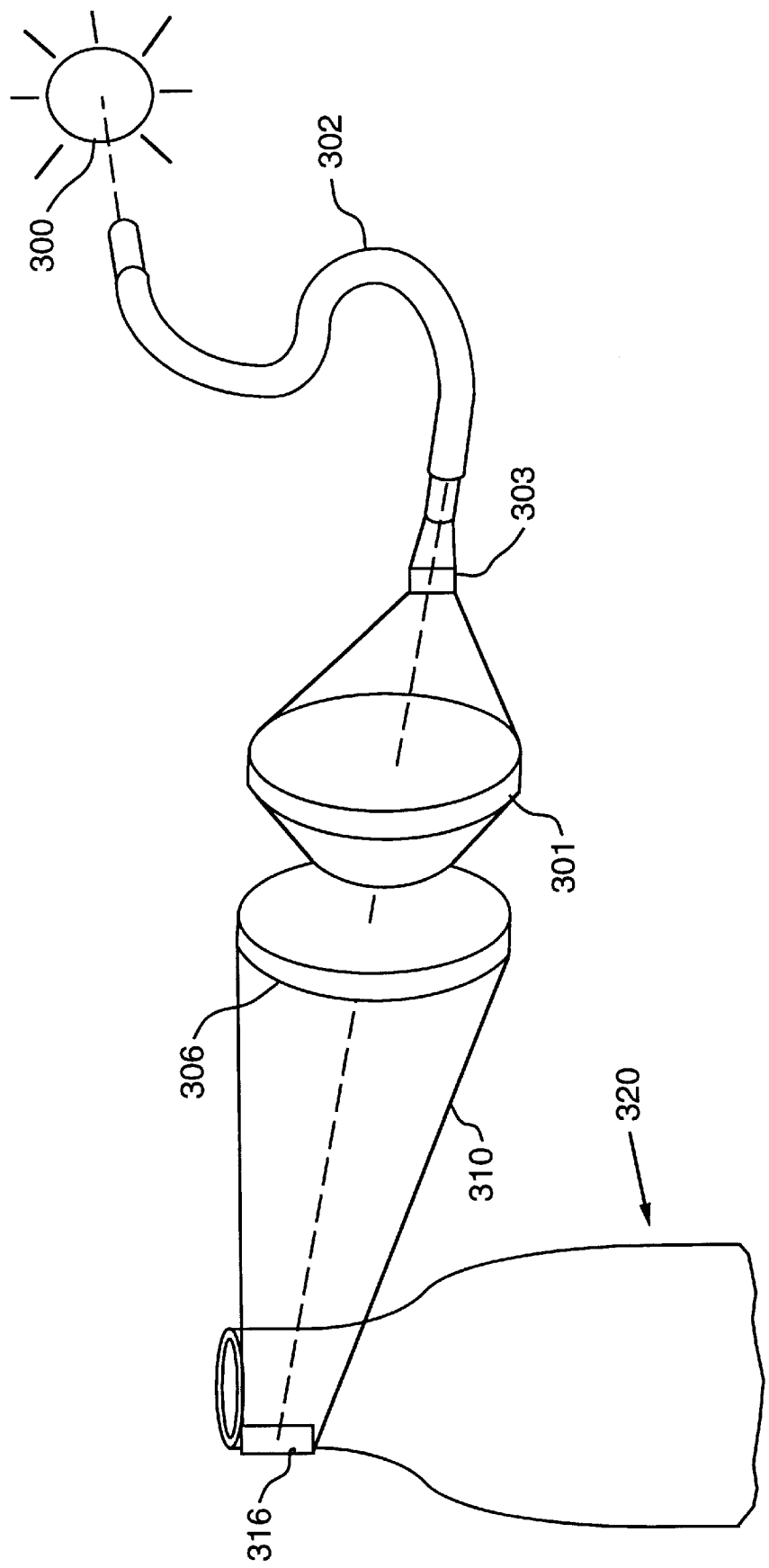
FIG. 7 is a schematic illustration showing a light source and related glass container portion which is being inspected.

Referring to FIG. 7, there is shown a preferred means for providing pulsed light tangentially to the finish of a glass container being inspected for vertical checks and related diagonal checks. A Xenon strobe lamp 300 has its output pass through fiberoptic bundle 302 through diffuser 303, and through condenser lenses 301, 306 to provide a converging light beam 310 tangentially to a portion of the bottle finish 316 of bottle 320. As in this embodiment of the invention the impinging light will pass through only a portion of the circumference of the glass finish, which may be on the order of 90 or 100 degrees, it will be preferred to employ a plurality of vertical inspection units to obtain complete circumferential inspection. As a result, the microprocessor 262 will control the pulsing of the light so that the initial light beam 310 is on only when other light beams are not on so as to avoid interference therebetween.

Figure 8:
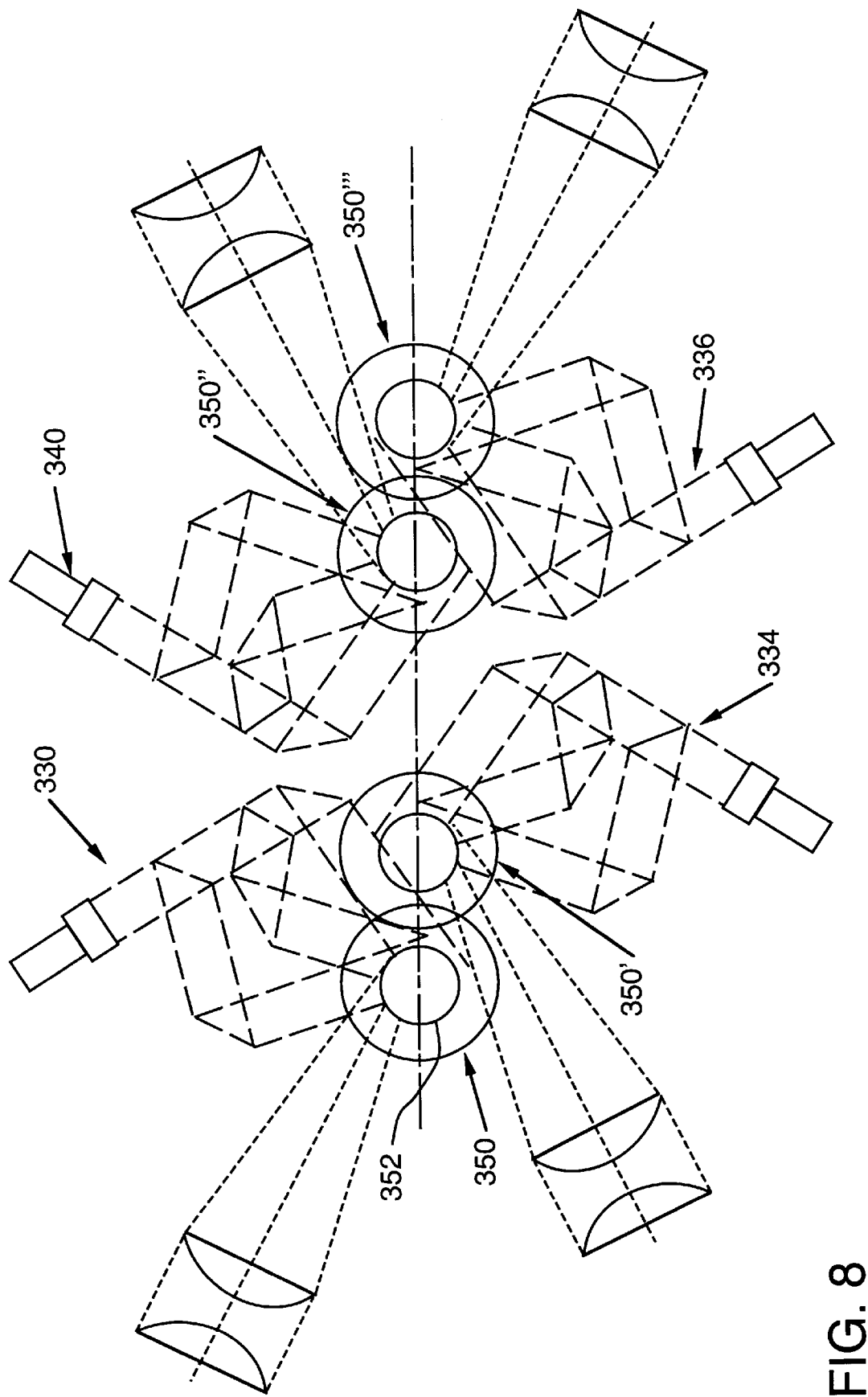
FIG. 8 is a plan view of a multiple inspection system for inspecting vertical and related diagonal checks.

Referring to FIG. 8, a system wherein four vertical inspection means designated generally by reference numbers 330, 334, 336 and 340 is shown with a bottle 350 shown in its initial position wherein a 90 degree arc of the finish 352 is being inspected by inspection means 330. After that, the bottle is transported to position 350' wherein it is inspected by inspection means 334 which inspects another circumferential portion of the finish. The bottle is then transported to position 350" wherein it is inspected by inspection means 340 and finally, it moves to position 350''' wherein the finish is inspected by system 336. Each system may be essentially a duplicate of the system shown in FIG. 6. It will be appreciated that in this manner, sequential inspection for vertical checks and related diagonal checks is accomplished without requiring axial rotation of the container.

Figure 9:
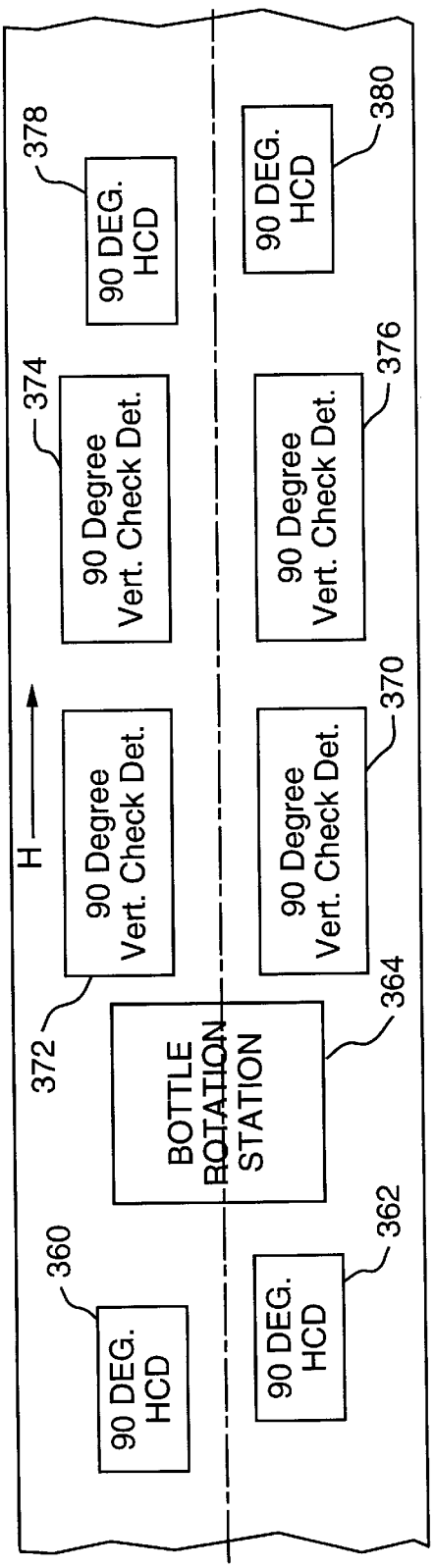
FIG. 9 is a schematic illustration showing one form of inspection system of the present invention adapted to inspect for horizontal, vertical and diagonal checks.

Referring to FIG. 9, a system will be considered wherein both the horizontal check inspection and the vertical check inspection are employed with each individual unit inspecting 90 degrees of the circumference of the container finish. Assuming that the containers are moving in the direction indicated by arrow H, the first phase of inspection would involve a 90 degree horizontal inspection 360 and the second phase would be a 90 degree horizontal inspection 362 which is later in time so that the pulsed light beams would not be on at the same time. The bottle would then enter a bottle rotating station wherein the bottle would be rotated 90 degrees. After that, in staggered fashion so that no two pulsed light beams are on at the same time, four phases of vertical check inspections 370, 372, 374, 376, each of 90 degrees, thereby covering the full 360 degrees circumference of the container finish would be effected. The remaining two 90 degree horizontal check inspections 378, 380 would then be performed. In this manner, the container would be inspected throughout its 360 degree circumference by the horizontal and related diagonal inspection means, as well as the vertical and related diagonal inspection means.

Figure 10:
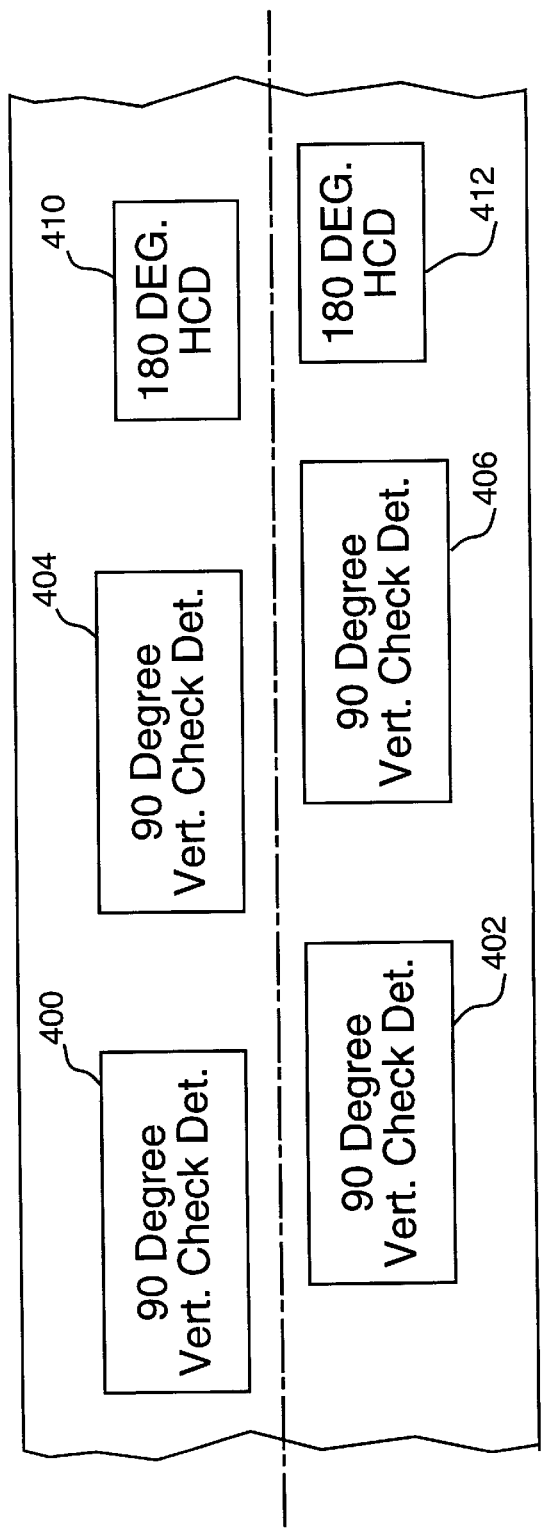
FIG. 10 is a schematic illustration similar to FIG. 9, but showing a different arrangement for inspecting horizontal, vertical and diagonal checks.

In the embodiment shown in FIG. 10, the inspection would not require rotation of the container. A series of four staggered vertical check inspections 400, 402, 404, 406 would be performed followed by two staggered horizontal check inspections 410, 412. In this manner, the full 360 degrees of the container would be inspected without requiring rotation as to either the horizontal inspection or vertical inspection.

Figure 11:
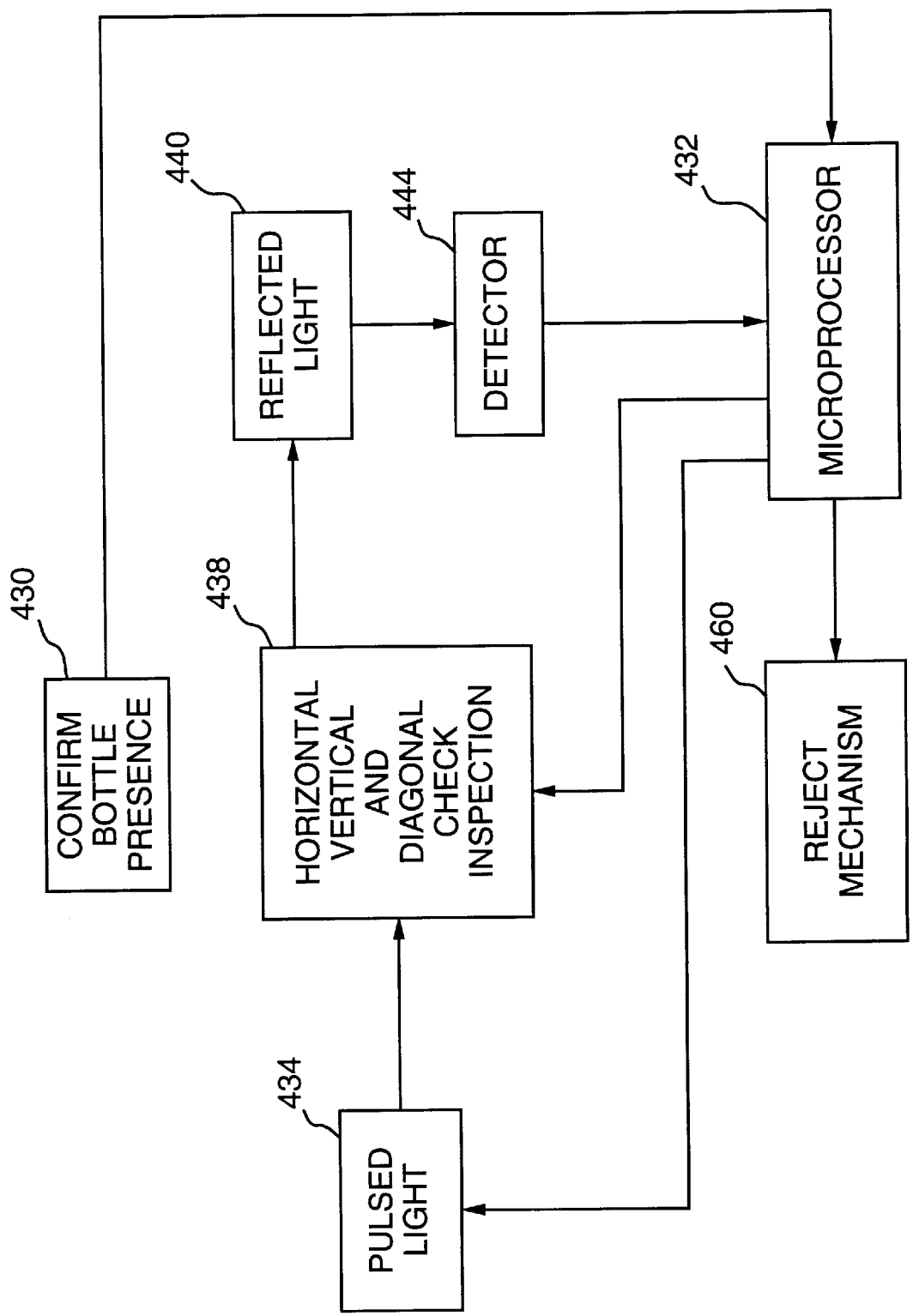
FIG. 11 is a schematic illustration of a system of the present invention.

Referring to FIG. 11, there is shown a schematic diagram of operation of a form of inspection system of the present invention. Initially, as the containers are moving along the conveyor, a signal would be provided to confirm that the bottle or other container is present at the inspection station 430. This would be received in the microprocessor 432 which would send out a signal to the pulsed light source 434 to provide the programmed pulsed light sequence to the reflectors which deliver the light beam to the exterior of the finish of the bottle located in the inspection station 438. The reflected light 440 would be delivered to detector 444 which would convert the light received into corresponding electrical signals which are delivered to microprocessor 432 which makes the above-described comparison. In the event that the comparison results in rejection based upon the check level exceeding the program threshold, a signal would be sent to the reject mechanism 460 to cause the container to be removed from the conveyor. The microprocessor 432 would also at the appropriate time send a signal to the inspection station 438 to trigger operation thereof. The operation may be a multi-step operation as in the cases of FIGS. 9 and 10 or might be a single operation in the case of the embodiment shown in FIG. 3 wherein the inspection will be performed in a unitary manner throughout the 360 degree circumference.

Figure 12:
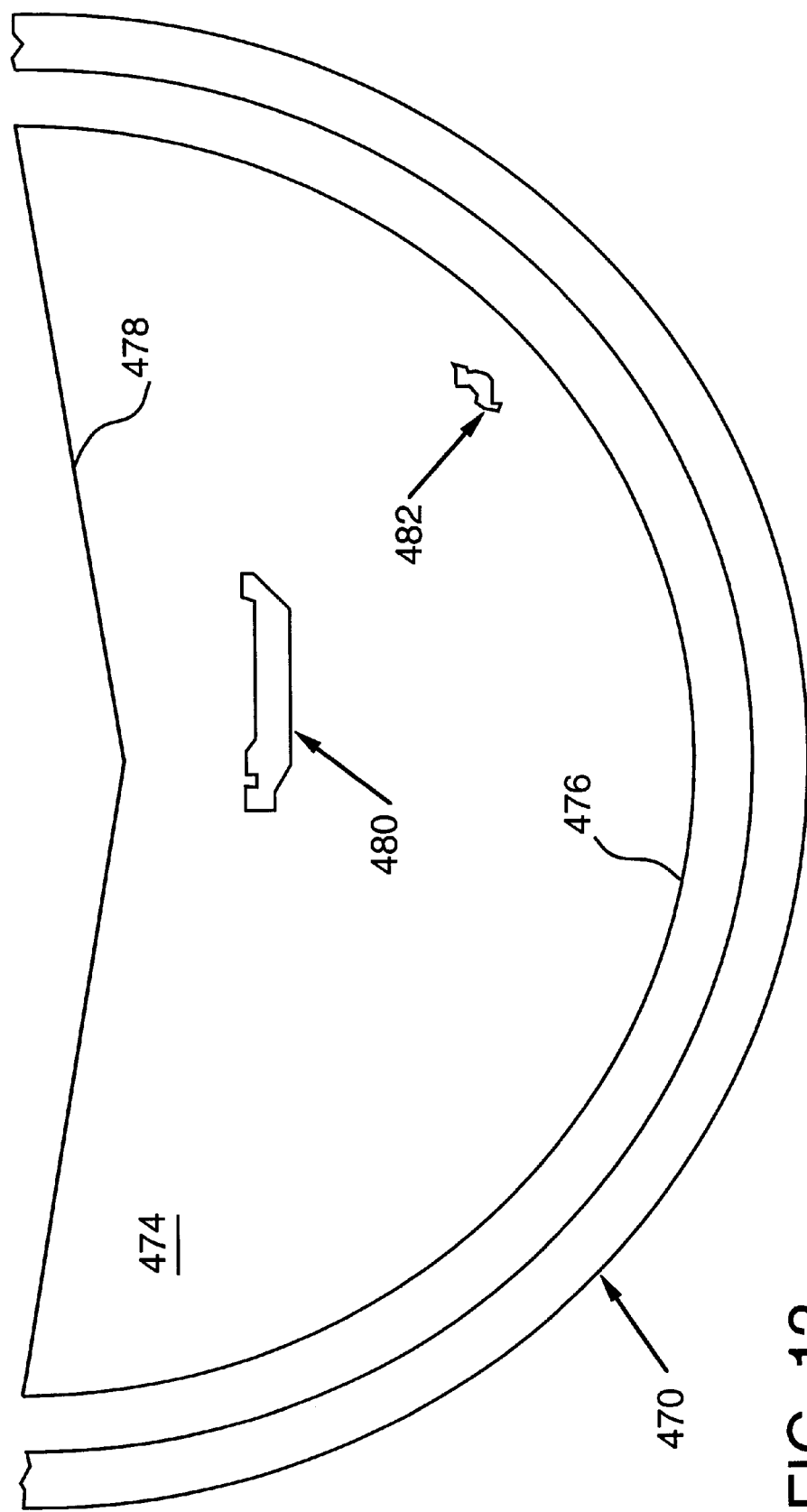
FIG. 12 is a partial illustration of a form of image obtainable with inspection systems of the present invention.

Referring to FIG. 12, there is shown an illuminated portion 470 of a container finish as seen by the horizontal system detector means. The region of interest 474 is shown by the closed figure having a semi-circular lower portion 476 and a generally V-shaped upper portion 478. In this manner, the sealing surface along 470 is not included within what the microprocessor obtains by way of reflected light. Reflected light 480, 482 indicating the presence of checks is shown by the islands. As other portions of the circumference of the sealing finish are inspected, a similar geometric relationship would be established.

While for simplicity of disclosure reference has been made herein to using a reject mechanism to remove containers which do not pass the check inspection, other means may also be employed. For example, a visual or audible alarm or system shutdown may be effected. Data regarding the inspections may be displayed, provided on hard copy, or stored with or without data processing. Such data may, for example, include reject statistics, last reject data, and trending of mold correlations.

It will be appreciated, therefore, that the present invention has provided an effective means for rapidly and automatically inspecting glass containers, such as jars or bottles, for checks exceeding a certain threshold while eliminating distortion of the data based upon threads or lugs, sealing surfaces, takeout rings and other planned deformations. The method and apparatus for accomplishing this is consistent with existing glass container molding, annealing and handling apparatus.

Reference herein to words of orientation, such as "horizontal" or "vertical" or "diagonal" or similar terms are relative terms and are not limitations on the invention unless expressly stated at a specific location.

Whereas particular embodiments of the invention have been described herein for purposes of illustration, it will be evident to those skilled in the art that numerous variations of the details may be made without departing from the invention as defined in the appended claims.

What is claimed is:

1. A method of inspecting a glass container for checks comprising
   introducing said container into an inspection region,
   illuminating the exterior of the container finish around at least a portion of the circumference thereof,
   detecting escaping light piped in the interior of said container finish,
   comparing information provided by said detected light with a reference standard, and
   employing said comparison to determine whether checks exist in said glass container finish.

2. The method of inspecting of claim 1 including
   prior to effecting said comparison converting said detected light into corresponding electrical signals.

3. The method of inspecting of claim 2 including
   employing a microprocessor to effect said comparison, and
   introducing said electrical signals into said microprocessor.

4. The method of inspecting of claim 3 including
   rotating said container axially during a portion of said inspection.

5. The method of inspecting of claim 3 including
   employing first inspection means for inspecting said container for horizontal and related horizontal diagonal checks.

6. The method of inspecting of claim 3 including
   employing second inspection means for inspecting said container for vertical and related vertical diagonal checks.

7. A method of inspecting a glass container for checks comprising
   introducing said container into an inspection region,
   illuminating the exterior of the container finish around at least a portion of the circumference thereof,
   detecting escaping light piped in the interior of said container finish,
   comparing information provided by said detected light with a reference standard,
   employing said comparison to determine whether checks exist in said glass container finish,
   prior to effecting said comparison converting said detected light into corresponding electrical signals,
   employing a microprocessor to effect said comparison,
   introducing said electrical signals into said microprocessor, and
   omitting from said comparison light reflected from threads, lugs, sealing surfaces, and takeout rings.

8. The method of inspecting of claim 2 including
   emitting from said microprocessor a reject signal to reject a said glass container having checks in excess of a predetermined size.

9. The method of inspecting of claim 8 including
   establishing in said microprocessor a threshold check value below which a reject signal will not be emitted.

10. The method of inspecting of claim 9 including
    providing container reject means for removing rejected containers when a reject signal is emitted by said microprocessor, and
    operating said reject mechanism to remove said container upon receipt of a said reject signal.

11. A method of inspecting a glass container for checks comprising
    introducing said container into an inspection region,
    illuminating the exterior of the container finish around at least a portion of the circumference thereof,
    detecting escaping light piped in the interior of said container finish,
    comparing information provided by said detected light with a reference standard,
    employing said comparison to determine whether checks exist in said glass container finish,
    prior to effecting said comparison converting said detected light into corresponding electrical signals,
    employing a microprocessor to effect said comparison,
    introducing said electrical signals into said microprocessor,
    employing first inspection means for inspecting said container for horizontal and related horizontal diagonal checks,
    providing reflector means interposed between a light source which provides said illumination in the form of a light beam and said glass container,
    directing said light beam onto said reflector means, and
    directing reflected light from said reflected means onto the region of said glass container being inspected.

12. The method of inspecting of claim 11 including
    directing said light beam onto said glass container finish exterior in an angularly downwardly direction.

13. The method of inspecting of claim 12 including
    employing an angle of about 45 to 55 degrees with respect to the vertical in directing said light beam angularly downwardly.

14. The method of inspecting of claim 12 including
    employing as said reflector means at least one reflector having a light receiving portion, a diffuser portion and a light emitting portion, and
    directing said light beam from said light emitting portion to said glass container.

15. The method of inspecting of claim 14 including
    said reflector means being a unitary generally conical reflector extending at least 180 degrees around said glass container finish.

16. The method of inspecting of claim 15 including
    employing as said reflector means a plurality of circumferentially spaced reflectors.

17. The method of inspecting of claim 15 including
employing as said conical reflector a conical reflector extending about 360 degrees around said glass container.
18. The method of inspecting of claim 14 including
employing as said reflector means at least one reflector which does not substantially increase the beam angle in the vertical plane but does increase the beam angle in the horizontal plane.
19. The method of inspecting of claim 14 including
employing as said light emitting portion a reflector having a toroidal configuration.
20. The method of inspecting of claim 15 including
employing a plurality of light sources circumferentially spaced around at least a portion of said glass container, and
directing said light beams generally radially in plane into said container finish.
21. The method of inspecting of claim 20 including
employing said process in inspecting a said container which is a glass bottle.
22. The method of inspecting of claim 5 including
detecting said reflected light with an electronic camera which converts said reflected light beam into corresponding electrical signals.
23. The method of inspecting of claim 22 including
focusing said reflected light onto said electric camera with lens means.
24. A method of inspecting a glass container for checks comprising
introducing said container into an inspection region,
illuminating the exterior of the container finish around at least a portion of the circumference thereof,
detecting escaping light piped in the interior of said container finish,
comparing information provided by said detected light with a reference standard,
employing said comparison to determine whether checks exist in said glass container finish,
prior to effecting said comparison converting said detected light into corresponding electrical signals,
employing a microprocessor to effect said comparison,
introducing said electrical signals into said microprocessor,
employing first inspection means for inspecting said container for horizontal and related horizontal diagonal checks, and
employing a plurality of first inspection means each of which inspects a portion of the circumference of said container finish.
25. The method of inspecting of claim 24 including
inspecting about 360 degrees of said container by said plurality of said first inspection means.
26. The method of inspecting of claim 25 including
employing two said first inspection means with each one inspecting about 180 degrees of the circumference of said container.
27. The method of inspecting of claim 25 including
employing more than two said first inspection means with each one inspecting less than 180 degrees of the circumference of said container.
28. The method of inspecting of claim 25 including
performing said inspection without rotation of said container.

29. The method of inspecting of claim 27 including
effecting rotation of said container after inspection thereof by at least one said first inspection means, but before inspection by the last said first inspection means.
30. The method of inspecting of claim 5 including
providing said light beams as pulsed beams.
31. The method of inspecting of claim 30 including
employing fiber optic means in delivering said light beams to said reflector means.
32. A method of inspecting a glass container for checks comprising
introducing said container into an inspection region,
illuminating the exterior of the container finish around at least a portion of the circumference thereof,
detecting escaping light piped in the interior of said container finish,
comparing information provided by said detected light with a reference standard,
employing said comparison to determine whether checks exist in said glass container finish,
prior to effecting said comparison converting said detected light into corresponding electrical signals,
employing a microprocessor to effect said comparison,
introducing said electrical signals into said microprocessor,
employing first inspection means for inspecting said container for horizontal and related horizontal diagonal checks, and
employing second inspection means for inspecting said container for vertical and related vertical diagonal checks.
33. The method of inspecting of claim 32 including
employing a plurality of said second inspection means each inspecting a portion of the circumference of said container finish.
34. The method of inspecting of claim 33 including
effecting said inspection by said second inspection means before, after or between inspection by said first inspection means.
35. The method of inspection of claim 5 including
employing said first inspection means for inspecting said related horizontal diagonal checks at an angle of up to about 40 degrees with respect to the horizontal.
36. The method of inspection of claim 32 including
employing said second inspection means for inspecting said related vertical diagonal checks at an angle of up to about 70 degrees with respect to the vertical.
37. The method of inspection of claim 36 including
employing said first inspection means for inspecting said related horizontal diagonal checks at an angle of up to about 40 degrees with respect to the horizontal.
38. A method of inspecting a glass container for checks comprising
introducing said container into an inspection region,
illuminating the exterior of the container finish around at least a portion of the circumference thereof,
detecting escaping light piped in the interior of said container finish,
comparing information provided by said detected light with a reference standard,
employing said comparison to determine whether checks exist in said glass container finish,
prior to effecting said comparison converting said detected light into corresponding electrical signals, employing a microprocessor to effect said comparison, introducing said electrical signals into said microprocessor, employing first inspection means for inspecting said container for horizontal and related horizontal diagonal checks, employing second inspection means for inspecting said container for vertical and related vertical diagonal checks, and employing overlap in the angular region of inspection for said related horizontal diagonal checks with the angular region of inspection for said related vertical diagonal checks.

39. The method of inspecting of claim 6 including illuminating a portion of the finish of said container by a light beam which impinges on said finish generally tangentially.

40. The method of inspecting of claim 39 including causing said light beam to impinge simultaneously on about 60 to 90 degrees of the circumference of said container.

41. A method of inspecting a glass container for checks comprising introducing said container into an inspection region, illuminating the exterior of the container finish around at least a portion of the circumference thereof, detecting escaping light piped in the interior of said container finish, comparing information provided by said detected light with a reference standard, employing said comparison to determine whether checks exist in said glass container finish, prior to effecting said comparison converting said detected light into corresponding electrical signals, employing a microprocessor to effect said comparison, introducing said electrical signals into said microprocessor, employing second inspection means for inspecting said container for vertical and related vertical diagonal checks, illuminating a portion of the finish of said container by a light beam which impinges on said finish generally tangentially, and employing a plurality of said second inspection means for inspecting the container finish.

42. The method of inspecting of claim 40 including delivering said detected continuous circumferential finish reflected light to detector means which effect conversion of said reflected light to corresponding electrical signals.

43. A method of inspecting a glass container for checks comprising introducing said container into an inspection region illuminating the exterior of the container finish around at least a portion of the circumference thereof, detecting escaping light piped in the interior of said container finish, comparing information provided by said detected light with a reference standard, employing said comparison to determine whether checks exist in said glass container finish, prior to effecting said comparison converting said detected light into corresponding electrical signals, employing a microprocessor to effect said comparison, introducing said electrical signals into said microprocessor, employing second inspection means for inspecting said container for vertical and related vertical diagonal checks, illuminating a portion of the finish of said container by a light beam which impinges on said finish generally tangentially, causing said light beam to impinge simultaneously on about 60 to 90 degrees of the circumference of said container, and passing said reflected light through at least one beam splitter prior to delivering said reflected light to said detector means.

44. A method of inspecting a glass container for checks comprising introducing said container into an inspection region, illuminating the exterior of the container finish around at least a portion of the circumference thereof, detecting escaping light piped in the interior of said container finish, comparing information provided by said detected light with a reference standard, employing said comparison to determine whether checks exist in said glass container finish, prior to effecting said comparison converting said detected light into corresponding electrical signals, employing a microprocessor to effect said comparison, introducing said electrical signals into said microprocessor, employing second inspection means for inspecting said container for vertical and related vertical diagonal checks, illuminating a portion of the finish of said container by a light beam which impinges on said finish generally tangentially, causing said light beam to impinge simultaneously on about 60 to 90 degrees of the circumference of said container, delivering said detected continuous circumferential finish reflected light to detector means which effect conversion of said reflected light to corresponding electrical signals, and directing the output of said beam splitter to said detector means by mirror means.

45. The method of inspecting of claim 44 including employing an electronic camera in said detector means.

46. The method of inspecting of claim 45 including employing lens means in said detector means to focus the light reflected from said mirrors onto said electronic camera.

47. The method of inspecting of claim 46 including employing a plurality of splitters, and having a mirror operatively associated with each said beam splitter.

48. The method of inspecting of claim 47 including combining the light beams emerging from each said beam splitter before introducing them into said electronic camera.

49. The method of inspecting of claim 41 including employing four said second inspection means.

50. The method of inspecting of claim 43 including directing said reflected light to said beam splitter by mirrors.

51. The method of inspecting of claim 46 including performing said inspection without requiring rotation of said container.

52. The method of inspecting of claim 47 including directing light reflected from the outer surface of said container finish away from said mirrors, whereby said light will not be delivered to said electronic camera.

53. The method of inspecting of claim 47 including employing said process to inspect containers which are bottles.

54. The method of inspecting of claim 47 including employing a pulsed light source to provide said light beam.

55. The method of inspecting of claim 54 including focusing said light beams on said container finish by lens means.

56. A method of inspecting a glass container for checks comprising introducing said container into an inspection region, illuminating the exterior of the container finish around at least a portion of the circumference thereof, detecting escaping light piped in the interior of said container finish, comparing information provided by said detected light with a reference standard, employing said comparison to determine whether checks exist in said glass container finish, prior to effecting said comparison converting said detected light into corresponding electrical signals, employing a microprocessor to effect said comparison, introducing said electrical signals into said microprocessor, employing second inspection means for inspecting said container for vertical and related vertical diagonal checks, illuminating a portion of the finish of said container by a light beam which impinges on said finish generally tangentially, and employing two said second inspection means, and inspecting about 170–190 degrees of said circumferential finish circumference with each.

57. The method of inspecting of claim 56 including positioning detector means for receiving reflected light at a higher elevation than the container.

58. The method of inspecting of claim 40 including employing first inspection means for inspecting said container for horizontal and related horizontal diagonal checks.

59. A method of inspecting a glass container for checks comprising introducing said container into an inspection region, illuminating the exterior of the container finish around at least a portion of the circumference thereof, detecting escaping light piped in the interior of said container finish, comparing information provided by said detected light with a reference standard, employing said comparison to determine whether checks exist in said glass container finish, prior to effecting said comparison converting said detected light into corresponding electrical signals, employing a microprocessor to effect said comparison, introducing said electrical signals into said microprocessor, employing second inspection means for inspecting said container for vertical and related vertical diagonal checks, illuminating a portion of the finish of said container by a light beam which impinges on said finish generally tangentially, causing said light beam to impinge simultaneously on about 60 to 90 degrees of the circumference of said container, employing first inspection means for inspecting said container for horizontal and related horizontal diagonal checks, employing a plurality of said first inspection means, and employing a plurality of said second inspection means.

60. The method of inspecting of claim 59 including pulsing said light beams, and pulsing the light beam for said second inspection means at a time different from said pulsing of said light beam for said first inspection means.

61. The method of inspecting of claim 59 including inspecting a portion of said circumferential container finish with each said first inspection means, and inspecting a portion of said container finish with each said second inspection means.

62. The method of inspecting of claim 61 including employing a generally conical reflector with each said first inspection means.

63. The method of inspecting of claim 61 including axially rotating said container during at least a portion of the cycle of inspection of said container.

64. The method of inspecting of claim 61 including effecting said inspection without requiring rotation of said container.

65. Apparatus for inspecting a glass container for checks comprising light source means for creating and delivering light beams, means for receiving said light beams and causing them to impinge on at least a portion of the exterior of said container finish circumference, detector means for receiving reflected light from the interior of said container finish, converting said interior reflected light into corresponding electrical signals, and microprocessor means for receiving said electrical signals from said detector means and comparing them with desired values to determine if the container finish should be rejected on the basis of the presence of checks.

66. The inspection apparatus of claim 65 including first inspection means for inspecting said container finish for horizontal checks and related horizontal diagonal checks.

67. Apparatus for inspecting a glass container for checks comprising light source means for creating and delivering light beams, means for receiving said light beams and causing them to impinge on at least a portion of the exterior of said container finish circumference, detector means for receiving reflected light from the interior of said container finish, converting said interior reflected light into corresponding electrical signals, microprocessor means for receiving said electrical signals from said detector means and comparing them with desired values to determine if the container finish should be rejected on the basis of the presence of checks, and second inspection means for inspecting said container for vertical and related vertical diagonal checks.

68. Apparatus for inspecting a glass container for checks comprising light source means for creating and delivering light beams, means for receiving said light beams and causing them to impinge on at least a portion of the exterior of said container finish circumference, detector means for receiving reflected light from the interior of said container finish, converting said interior reflected light into corresponding electrical signals, microprocessor means for receiving said electrical signals from said detector means and comparing them with desired values to determine if the container finish should be rejected on the basis of the presence of checks, first inspection means for inspecting said container finish for horizontal and related horizontal diagonal checks, and second inspection means for inspecting said container for vertical and related vertical diagonal checks.

69. Apparatus for inspecting a glass container for checks comprising light source means for creating and delivering light beams, means for receiving said light beams and causing them to impinge on at least a portion of the exterior of said container finish circumference, detector means for receiving reflected light from the interior of said container finish, converting said interior reflected light into corresponding electrical signals, microprocessor means for receiving said electrical signals from said detector means and comparing them with desired values to determine if the container finish should be rejected on the basis of the presence of checks, first inspection means for inspecting said container finish for horizontal checks and related horizontal diagonal checks, and means for excluding from said comparison intentionally created deformations in said container finish.

70. The inspection apparatus of claim 69 including said intentionally created deformations including at least one category of deformation selected from the group consisting of threads, lugs, takeout rings, sealing surfaces and mold seams.

71. The inspection apparatus of claim 65 including a conveyor for transporting said containers through an inspection zone, and reject means for receiving a signal from said microprocessor for a container to be rejected on the basis of the presence of unacceptable checks and withdrawing said container from said conveyor.

72. The inspection apparatus of claim 71 including said microprocessor means having a threshold value below which a reject signal will not be emitted.

73. The inspection apparatus of claim 65 including said reflector means being a unitary for receiving said light beams structured to extend for 360 degrees around said container.

74. The inspection apparatus of claim 72 including said reflector means having a plurality of circumferentially extending cooperating for receiving said light beams elements in the aggregate extending about 360 degrees.

75. The inspection apparatus of claim 74 including said reflector being a generally conical reflector having an entry portion, a diffuser portion and a toroidal reflector which directs said light beam onto the exterior finish of said container.

76. The inspection apparatus of claim 75 including said toroidal surface directing said light beam generally angularly downwardly toward said container exterior finish.

77. The inspection apparatus of claim 73 including said toroidal surface directing said light beam downwardly and angularly at an angle of about 45 to 55 degrees with respect to the vertical.

78. The inspection apparatus of claim 65 including said means for receiving light beams being reflector means structured so as to not substantially increase the beam angle in the vertical plane, but increase the beam angle in the horizontal plane.

79. The inspection apparatus of claim 78 including said light source means including a plurality of light sources spaced circumferentially around at least a portion of said glass container finish.

80. The inspection apparatus of claim 65 including said means for receiving light beams being reflector means directing said light beams generally radially onto the exterior of said container finish.

81. The inspection apparatus of claim 65 including said apparatus being structured to inspect a glass container which is a bottle.

82. The inspection apparatus of claim 81 including said detector means including means selected from the group consisting of charge coupled devices, an electronic camera, and a photodiode detector.

83. The inspection apparatus of claim 66 including said detector means including a lens for focusing the reflected light beam onto said CCD electronic camera or a single photodiode.

84. Apparatus for inspecting a glass container for checks comprising light source means for creating and delivering light beams, means for receiving said light beams and causing them to impinge on at least a portion of the exterior of said container finish circumference, detector means for receiving reflected light from the interior of said container finish, converting said interior reflected light into corresponding electrical signals, microprocessor means for receiving said electrical signals from said detector means and comparing them with desired values to determine if the container finish should be rejected on the basis of the presence of checks, first inspection means for inspecting said container finish for horizontal checks and related horizontal diagonal checks, said detector means including a lens for focusing the reflected light beam onto said CCD electronic camera or a single photodiode, and employing a plurality of said first inspection means in inspecting said container finish.

85. The inspection apparatus of claim 67 including rotating means for rotating said container axially after an inspection by one inspection means.

86. The inspection apparatus of claim 67 including employing a plurality of said second inspection means.

87. The inspection apparatus of claim 86 including providing a plurality of beam splitters which receive light reflected from the container, and reflecting means for reflecting each light beam onto said detector means.

88. The inspection apparatus of claim 86 including said reflector means including a first mirror, a second mirror and third mirror with each of said reflected light beams being directed toward said detector means by said first mirror.

89. The inspection apparatus of claim 88 including each said second inspection means inspecting a circumferential portion of said container finish.

90. The inspection apparatus of claim 68 including said light source means providing separate pulsed light beams for each of said second inspection means.

91. The inspection apparatus of claim 65 including said plurality of first inspection means and said plurality of second inspection means each inspecting a portion of said container, and said microprocessor means having means for controlling the operation of each said first and second inspection means so as to establish relative staggering of the inspection process.

92. The inspection apparatus of claim 65 including said means for receiving said light beams being reflector means.

* * * * *

UNITED STATES PATENT AND TRADEMARK OFFICE
CERTIFICATE OF CORRECTION

PATENT NO.    : 6,211,952 B1
DATED         : April 3, 2001
INVENTOR(S)   : Joseph G. Weiland et al.

It is certified that error appears in the above-identified patent and that said Letters Patent is hereby corrected as shown below:

Column 18,
Line 16, delete the first occurrence of "reflector", replace with
-- for receiving said light beams --.

Signed and Sealed this

Twentieth Day of August, 2002

Attest:

Attesting Officer

JAMES E. ROGAN
Director of the United States Patent and Trademark Office